United States Patent [19]
LeClercq

[11] Patent Number: 4,509,512
[45] Date of Patent: Apr. 9, 1985

[54] SUPPORT UNDERGARMENT FOR PENILE PROTHESIS IMPLANT PATIENT

[76] Inventor: Marion J. LeClercq, 2893 Knox Ave. S., Apt. 216, Minneapolis, Minn. 55408

[21] Appl. No.: 482,422

[22] Filed: Apr. 6, 1983

[51] Int. Cl.³ .............................................. A61F 5/40
[52] U.S. Cl. .................................................. 128/160
[58] Field of Search ............... 128/157, 158, 159, 160, 128/161; 2/78 R, 78 A, 78 D, 403

[56] References Cited
U.S. PATENT DOCUMENTS

| | | | |
|---|---|---|---|
| 3,207,155 | 9/1965 | Casey | 128/159 |
| 3,621,846 | 11/1971 | Lehman | 128/160 X |
| 4,195,630 | 4/1980 | Connery | 128/159 |
| 4,345,337 | 8/1982 | Chung | 128/159 X |

Primary Examiner—John D. Yasko
Attorney, Agent, or Firm—Robert E. Granrud

[57] ABSTRACT

Bikini-type undergarment of two triangular panels sewed together at apices have a pocket in the front panel for protectively supporting the continually erected penis of a penile prothesis implant patient.

11 Claims, 4 Drawing Figures

U.S. Patent  Apr. 9, 1985  4,509,512
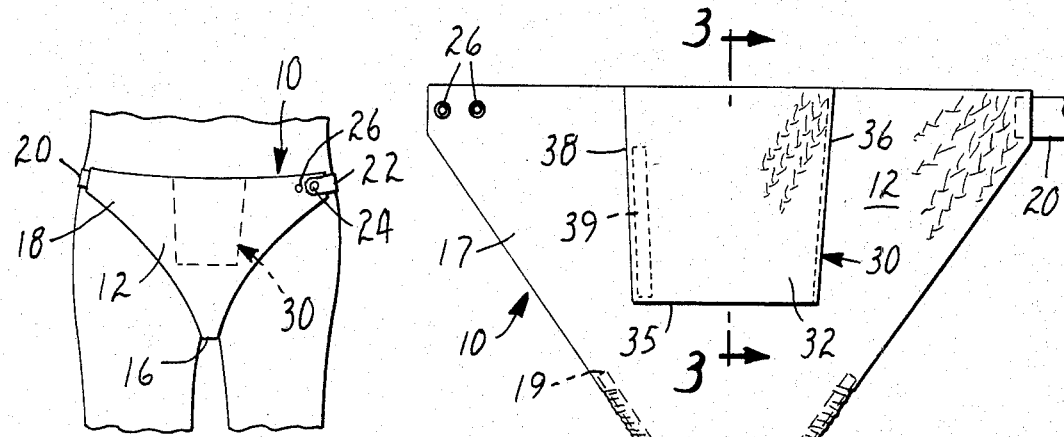
FIG. 1
FIG. 2
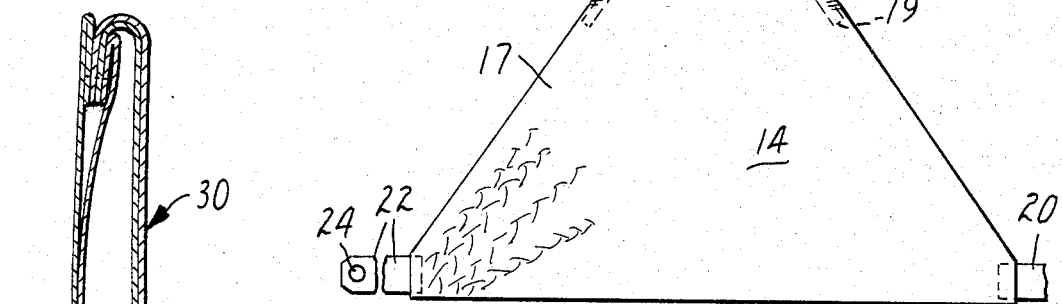
FIG. 3
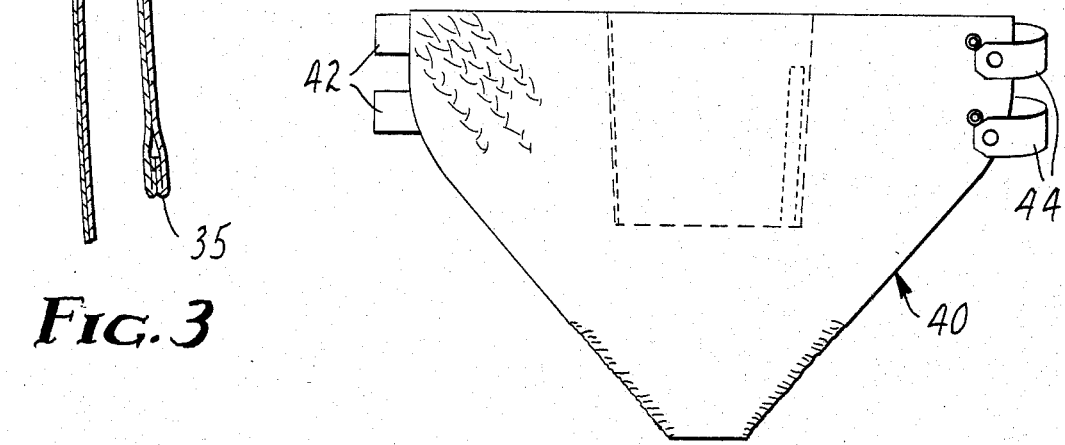
FIG. 4

4,509,512

SUPPORT UNDERGARMENT FOR PENILE PROTHESIS IMPLANT PATIENT

TECHNICAL FIELD

This invention relates to supportive, protective undergarments for men.

BACKGROUND ART

Men who are unable to achieve or maintain an erection may undergo a surgical procedure involving a rigid or semi-rigid penile implant which results in a continual erection. To cope with the pendulous nature of the erected penis, the usual undergarment has been an athletic supporter or the like, but the penis is too painful to tolerate the pressure applied by such an undergarment until the end of a convalescent period of about six weeks. No suitable, supportive undergarment has previously been available for use during that period. During the next several months, the pressure of an athletic supporter may be intolerably uncomfortable, so that some patients have tried women's panty girdles even though they are only partially effective for supporting an erected penis.

A penile implant also tends to make the penis highly sensitive to cold temperatures so that some patients wrap their penises in an effort to keep them warm, in spite of the inconvenience of repeated wrapping and unwrapping. Furthermore, the wrapping accentuates the bulkiness of the erected penis which by itself could produce an unsightly bulge in the patient's troussers.

DISCLOSURE OF INVENTION

The invention provides an undergarment that provides effective, comfortable protection and support for a continually erected penis, both during the painful convalescent period and during subsequent normal day-to-day activities. The novel undergarment is in the nature of bikini briefs in that it comprises triangular front and rear cloth panels connected together at apices to form a crotch. There are elastic bands puckering the edges of the panels in the vicinity of the crotch. A first parallel side of a trapezoidal cloth flap is permanently attached to the front panel along the top of the panel. One of its sides which are adjacent to said first side is permanently attached and the other is releasably attached to the front panel, while the second parallel side of the flap is open at the bottom to provide a pocket for the penis. The novel undergarment further includes means for fastening the top corners of said panels together around the wearer's waist with said flap between the wearer's abdomen and his waist.

Preferably the flap is wider at the top than at the bottom, and the opening at the bottom is from 3 to 4.5 inches (7.5 to 11.5 cm) in length, preferably about 4 inches (10 cm). This permits the penis to be inclined against either side of the pocket and hence not directly behind the trouser's fly, the thickness of which would tend to accentuate whatever bulge the penis makes in the trousers. The ability to rest the penis against one side or the other also enhances comfort. If the opening were less than 3 inches (7.5 cm), the penis would tend to be vertical and hence directly behind the fly. If the opening were more than 4.5 inches (11.5 cm), the penis might fall out of the pocket.

Preferably each of the front and rear panels is made of two layers of a supple, shape-retaining cloth, preferably cotton sheeting such as percale. This allows the seams and the elastic bands to be concealed, thus enhancing appearance and apparent quality. Double layers also provide better support and better thermal insulation over the penis. Preferably the flap has two cloth layers, and the layer facing the front panel should be soft for comfort such as cotton flannel which better holds heat from the body to keep the penis warm. The warmth of the penis is enhanced because the novel undergarment holds the penis closely against the abdomen. The other layer of the flap preferably is the same as that of the triangular panels such as cotton sheeting for durability and appearance.

BRIEF DESCRIPTION OF THE DRAWINGS

FIG. 1 shows an undergarment of the invention in use;

FIG. 2 shows the interior face of the undergarment of FIG. 1 opened and flattened;

FIG. 3 is an enlarged, partial cross-section along lines 3—3 of FIG. 2; and

FIG. 4 shows another embodiment of the invention.

The undergarment 10 shown in FIGS. 1, 2 and 3 comprises a triangular front panel 12 and a triangular rear panel 14 sewn together at apices to form a crotch 16. Each panel has two layers 17, 18 (FIG. 3) of cotton sheeting sewn together with concealed turned seams. While being fully stretched, two narrow elastic bands 19 have been sewn into those seams in the area of the crotch 16, thus providing form-fittiing puckering in the garment as worn. A short, wide elastic tape 20 (broken in FIG. 2) permanently connects the corners of the panels 12, 14 at one side of the undergarment 10. Another short, wide elastic tape 22 is sewn to the other corner of the rear panel 14 and carries a snap 24 that mates with one of the two snaps 26 at the free corner of the front panel 12.

A trapezoidal flap 30 is centrally attached to the inner surface of the front panel 12, forming an inverted pocket or pouch for receiving an erected penis. As best seen in FIG. 3, the flap 30 is also of double construction, its outer layer 32 being cotton sheeting and its inner layer 34 being cotton flannel. The layers 32 and 34 have a concealed turned seam at the open side 35 of the flap, and at the opposite side of the flap they are sewn across the top of the front panel 12 between its two layers 17, 18.

One vertical side 36 of the flap 30 is sewn to the front panel 12, and the opposite vertical side 38 is releasably attached to the front panel by hidden hook-and-loop fastener tapes 39 such as are sold under the trademark "Velcro". Preferably the softer of the fastener tapes is sewn to the flap since this is more likely to contact the penis when the flap is being opened and closed.

The undergarment 40 shown in FIG. 4 is similar to the undergarment 10 except that the corners of its triangular panels are connected by two sets of short, wide elastic tapes 42, 44. The two lower tapes provide enhanced support for the erected penis. Because pressure applied by those lower tapes would be uncomfortable to a convalescent, they would normally be left unfastened at that time. Since the undergarment 10 is slightly more economical, it is expected that hospitals will utilize the undergarment 10 while the patient will obtain the more versatile undergarment 40 for later use.

EXAMPLE

The undergarment 10 has been made to the following dimensions:

Panels 12,14: 15.75 in. (40 cm) across top and 13.25 in. (33.7 cm) from top to sewing at 16
Elastic bands 19: 7.75 in. (19.7 cm) fully stretched
Elastic tape 20: 2 in. (5 cm) unstretched exposed portion
Elastic tape 22: 2.1 in. (5.3 cm) unstretched exposed portion
In the undergarment 40:
Fastener tapes 44: 4 in. (10 cm) in length

I claim:

1. An undergarment for protecting and supporting a continually erected penis of a prothesis implant patient, which undergarment comprises triangular front and rear cloth panels connected together at apices to form a crotch, elastic bands puckering the edges of the panels in the vicinity of the crotch, a trapezoidal cloth flap with its first parallel side permanently attached to the front panel along the top of the panel, one of its sides which are adjacent to said first side being permanently and the other being releasably attached to the front panel, and its second parallel side being open at the bottom to provide a pocket for the erected penis, means for fastening the free corners of said panels together around the wearer's waist with said flap between the abdomen of the wearer and his penis.

2. Undergarment as defined in claim 1 wherein the flap is wider at the top than at the bottom, and the opening at the bottom is from 3 to 4.5 inches in length.

3. Undergarment as defined in claim 2 wherein the flap comprises two layers of cloth, the internal layer of which is a soft, thermally insulating fabric.

4. Undergarment as defined in claim 3 wherein the panels and external flap layer are cotton sheeting and the insulating fabric is cotton flannel.

5. Undergarment as defined in claim 4 wherein the front panel comprises two layers of cotton sheeting and the flap is stitched between those two layers at the top of the panel.

6. Undergarment as defined in claim 5 wherein the two flap layers have a concealed turned seam at the open side of the flap.

7. Undergarment as defined in claim 6 wherein at the releasably attached side of the flap are hook-and-loop fastener tapes.

8. Undergarment as defined in claim 1 wherein said fastening means comprises means permanently attaching two upper corners of the triangular panels together at one side of the undergarment and elastic tape releasably attaching the two upper corners at the other side of the undergarment.

9. Undergarment as defined in claim 8 wherein said elastic tape consists of two sets of tape, the lower of which can be left open for comfort or adjustably fastened to hold the penis snugly against the wearer's abdomen.

10. Undergarment as defined in claim 9 wherein each of the front triangular panel and the flap consists of double layers of cloth, and the interior layer of the flap is a thermally insulating fabric.

11. Undergarment as defined in claim 10 wherein both layers of the panel and the outer layer of the flap are cotton percale and the inner layer of the flap is cotton flannel.

* * * * *